(12) United States Patent
McFetridge

(10) Patent No.: US 11,911,278 B2
(45) Date of Patent: Feb. 27, 2024

(54) IMPLANT MATERIALS FOR TMJ REPAIR, METHODS OF MAKING THE IMPLANT MATERIALS FOR TMJ REPAIR, AND METHOD OF USING IMPLANT MATERIALS FOR TMJ REPAIR

(71) Applicant: University of Florida Research Foundation, Inc., Gainesville, FL (US)

(72) Inventor: Peter S. McFetridge, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 825 days.

(21) Appl. No.: 17/032,402

(22) Filed: Sep. 25, 2020

(65) Prior Publication Data

US 2021/0007850 A1 Jan. 14, 2021

Related U.S. Application Data

(62) Division of application No. 14/363,538, filed as application No. PCT/US2012/068385 on Dec. 7, 2012, now Pat. No. 10,828,165.

(60) Provisional application No. 61/568,733, filed on Dec. 9, 2011.

(51) Int. Cl.
*A61F 2/30* (2006.01)
*A61L 27/38* (2006.01)
*A61L 27/36* (2006.01)

(52) U.S. Cl.
CPC ........ *A61F 2/3099* (2013.01); *A61L 27/3612* (2013.01); *A61L 27/3662* (2013.01); *A61L 27/3687* (2013.01); *A61L 27/3691* (2013.01); *A61L 27/38* (2013.01); *A61L 27/386* (2013.01); *A61L 27/3834* (2013.01); *A61L 27/3886* (2013.01); *A61F 2002/30754* (2013.01); *A61L 2430/10* (2013.01); *A61L 2430/24* (2013.01); *A61L 2430/40* (2013.01)

(58) Field of Classification Search
None
See application file for complete search history.

(56) References Cited

U.S. PATENT DOCUMENTS

| | | |
|---|---|---|
| 2007/0254005 A1 | 11/2007 | Pathak et al. |
| 2008/0195211 A1 | 8/2008 | Lin et al. |
| 2010/0028396 A1 | 2/2010 | Ward et al. |
| 2010/0168856 A1 | 7/2010 | Long et al. |
| 2011/0009963 A1 | 1/2011 | Francois et al. |

OTHER PUBLICATIONS

Lumpkins, S.; McFetridge, P. Regional variations in the viscoelastic compressive properties of the temporomandibular joint disc and implications toward tissue engineering. Journal of Biomedical Materials Research Part a, p. 784-791, Sep. 1, 2009 2009. ISSN 1549-3296.

(Continued)

*Primary Examiner* — Javier G Blanco
(74) *Attorney, Agent, or Firm* — Thomas Horstemeyer LLP.

(57) ABSTRACT

In accordance with the purpose(s) of the present disclosure, as embodied and broadly described herein, embodiments of the present disclosure, in one aspect, relate to TMJ implantation materials and implants (e.g., temporomandibular joint (TMJ) disc), methods of making TMJ implantation materials and implants, methods of forming a TMJ implantation material or an implant, and the like.

15 Claims, 6 Drawing Sheets

(56) References Cited

OTHER PUBLICATIONS

Lumpkins, S.; Pierre, N.; McFetridge, P. A mechanical evaluation of three decellularization methods in the design of a xenogeneic scaffold for tissue engineering the temporomandibular joint disc. Acta Biomaterialia, p. 808-816, Jul. 2008 2008. ISSN 1742-7061.

Tanaka, E.; Koolstra, J. Biomechanics of the Temporomandibular Joint. Journal of Dental Research, p. 989-991, Nov. 2008 2008. ISSN 0022-0345.

Dolwick, M. Discectomy as an effective treatment for painful temporomandibular joint internal derangement: A 5-year clinical and radiographic follow-up. Journal of Oral and Maxillofacial Surgery, p. 758-759, Jul. 2001 2001. ISSN 0278-2391.

Abramowicz, S. et al. Temporomandibular joint reconstruction after failed teflon-proplast implant: case report and literature review. International Journal of Oral and Maxillofacial Surgery, p. 763-767, Aug. 2008 2008. ISSN 0901-5027.

Dimitroulis, G.; Dolwick, M. Temporomandibular disorders .3. Surgical treatment. Australian Dental Journal, p. 16-20, Feb. 1996 1996. ISSN 0045-0421.

Wilkes, C. Surgical-Treatment of Internal Derangements of the Temporomandibular-Joint—A Long-Term Study. Archives of Otolaryngology-Head & Neck Surgery, p. 64-72, Jan. 1991 1991. ISSN 0886-4470.

Almarza, A.; Athanasiou, K. Design characteristics for the tissue engineering of cartilaginous tissues. Annals of Biomedical Engineering, p. 2-17, Jan. 2004 2004. ISSN 0090-6964.

McFetridge, P. et al. Endothelial and smooth muscle cell seeding onto processed ex vivo arterial scaffolds using 3D vascular bioreactors. Asaio Journal, p. 591-600, Nov.-Dec. 2004 2004. ISSN 1058-2916.

McFetridge, P. et al. Preparation of porcine carotid arteries for vascular tissue engineering applications. Journal of Biomedical Materials Research Part a, p. 224-234, Aug. 1, 2004 2004. ISSN 0021-9304.

Athanasiou, K. A. Tissue engineering of temporomandibular joint cartilage. San Rafael, Calif. (1537 Fourth Street, San Rafael, CA 94901 USA): Morgan & Claypool Publishers: 1 electronic text (xi, 108 p. p. 2009.

Koolstra, J.; Tanaka, E. Tensile stress patterns predicted in the articular disc of the human temporomandibular joint. Journal of Anatomy, p. 411-416, Oct. 2009 2009. ISSN 0021-8782.

Singh, M.; Detamore, M. Tensile properties of the mandibular condylar cartilage. Journal of Biomechanical Engineering-Transactions of the Asme, p. -, Feb. 2008 2008. ISSN 0148-0731.

Snider, G. et al. Regional Dynamic Tensile Properties of the TMJ Disc. Journal of Dental Research, p. 1053-1057, Nov. 2008 2008. ISSN 0022-0345.

Beek, M. et al. Dynamic properties of the human temporomandibular joint disc. Journal of Dental Research, p. 876-880, Mar. 2001 2001. ISSN 0022-0345.

Francis, K.; Palsson, B. Effective intercellular communication distances are determined by the relative time constants for cyto/chemokine secretion and diffusion. Proceedings of the National Academy of Sciences of the United States of America, p. 12258-12262, Nov. 11, 1997 1997. ISSN 0027-8424.

Beek, M.; Koolstra, J.; Van Eijden, T. Human temporomandibular joint disc cartilage as a poroelastic material. Clinical Biomechanics, p. 69-76, Jan. 2003 2003. ISSN 0268-0033.

Rau, K. et al. Investigation of laser-induced cell lysis using time-resolved imaging. Applied Physics Letters, v. 84, n. 15, p. 2940-2942, Apr. 12, 2004 2004. ISSN 0003-6951.

Venugopalan, V. et al. Role of laser-induced plasma formation in pulsed cellular microsurgery and micromanipulation. Physical Review Letters, v. 88, n. 7, p. -, Feb. 18, 2002 2002. ISSN 0031-9007.

Vogel, A.; Venugopalan, V. Mechanisms of pulsed laser ablation of biological tissues (vol. 103, p. 577, 2003). Chemical Reviews, v. 103, n. 5, p. 2079-2079, May 2003 2003. ISSN 0009-2665.

Byrne, D. et al. Simulation of tissue differentiation in a scaffold as a function of porosity, Young's modulus and dissolution rate: Application of mechanobiological models in tissue engineering. Biomaterials, p. 5544-5554, Dec. 2007 2007. ISSN 0142-9612.

Abousleiman, R. et al. The human umbilical vein: A novel scaffold for musculoskeletal soft tissue regeneration. Artificial Organs, v. 32, n. 9, p. 735-742, Sep. 2008 2008. ISSN 0160-564X.

Abousleiman, R. et al. Tendon Tissue Engineering Using Cell-Seeded Umbilical Veins Cultured in a Mechanical Stimulator. Tissue Engineering Part a, v. 15, n. 4, p. 787-795, Apr. 2009 2009. ISSN 1937-3341.

Villegas, C. Preparation of ex vivo-based biomaterials using convective flow decellularization., v. 15, n. 2, p. 191-200, 2009.

McFetridge, P. et al. Vascular tissue engineering: Bioreactor design considerations for extended culture of primary human vascular smooth muscle cells. Asaio Journal, p. 623-630, Sep.-Oct. 2007 2007. ISSN 1058-2916.

Crouzier, T. et al. Modification of Single Walled Carbon Nanotube Surface Chemistry to Improve Aqueous Solubility and Enhance Cellular Interactions. Langmuir, p. 13173-13181, Nov. 18, 2008 2008. ISSN 0743-7463.

Lahiji, K. et al. Cyclic strain stimulates proliferative capacity, alpha 2 and alpha 5 integrin, gene marker expression by human articular chondrocytes propagated on flexible silicone membranes. In Vitro Cellular & Developmental Biology-Animal, v. 40, n. 5-6, p. 138-142, May-Jun. 2004 2004. ISSN 1071-2690.

Blaze, M. et al. Brominated Tyrosine and Polyelectrolyte Multilayer Analysis by Laser Desorption Vacuum Ultraviolet Postionization and Secondary Ion Mass Spectrometry. Analytical Chemistry, v. 83, n. 12, p. 4962-4969, Jun. 15, 2011 2011. ISSN 0003-2700.

Dantas, M. et al. Improvement of dermal burn healing by combining sodium alginate/chitosan-based films and low level laser therapy. Journal of Photochemistry and Photobiology B-Biology, v. 105, n. 1, p. 51-59, Oct. 5, 2011 2011. ISSN 1011-1344.

Zmora, S.; Glicklis, R.; Cohen, S. Tailoring the pore architecture in 3-D alginate scaffolds by controlling the freezing regime during fabrication. Biomaterials, p. 4087-4094, Oct. 2002 2002. ISSN 0142-9612.

Bonnet, A. et al. Transcriptome profiling of sheep granulosa cells and oocytes during early follicular development obtained by Laser Capture Microdissection. Bmc Genomics, v. 12, p. -, Aug. 18, 2011 2011. ISSN 1471-2164.

Gao, W.; Zhang, W.; Meldrum, D. RT-qPCR based quantitative analysis of gene expression in single bacterial cells. Journal of Microbiological Methods, v. 85, n. 3, p. 221-227, Jun. 2011 2011. ISSN 0167-7012.

Gonzalez-Roca, E. et al. Accurate Expression Profiling of Very Small Cell Populations. Plos One, v. 5, n. 12, p. -, Dec. 28, 2010 2010. ISSN 1932-6203.

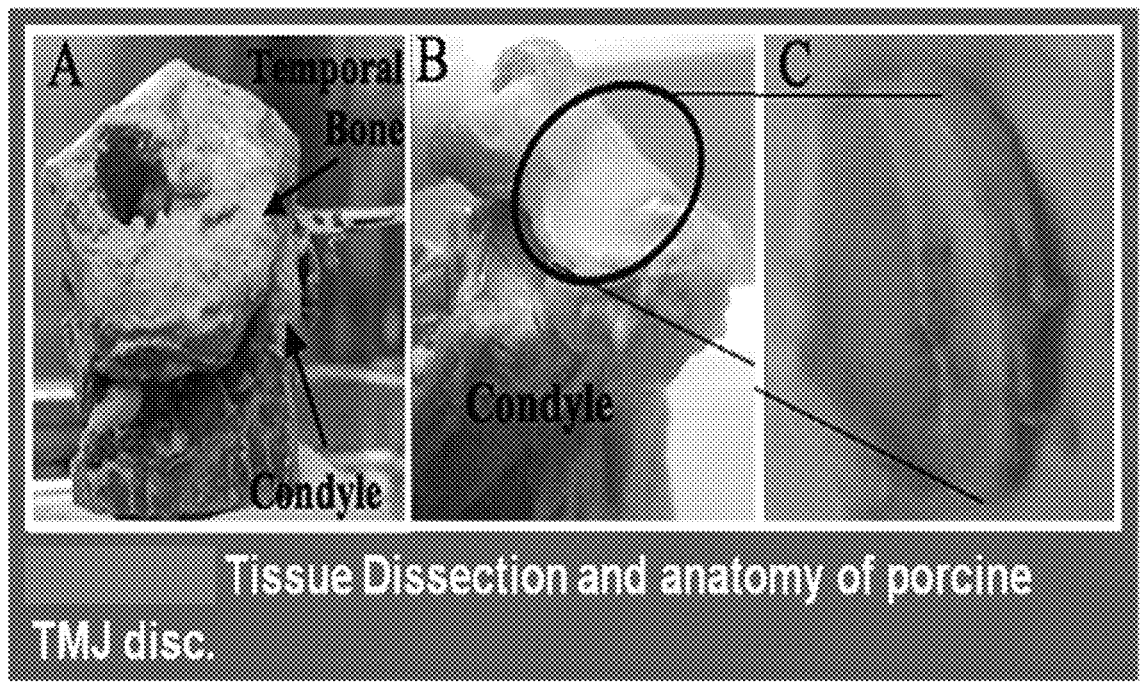
FIG. 1.1
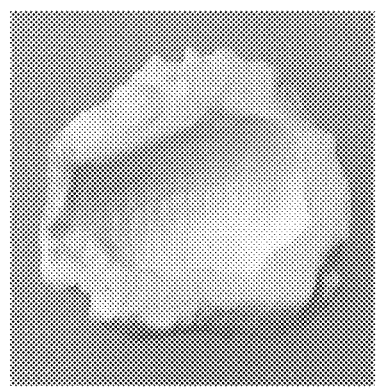
FIG. 1.2

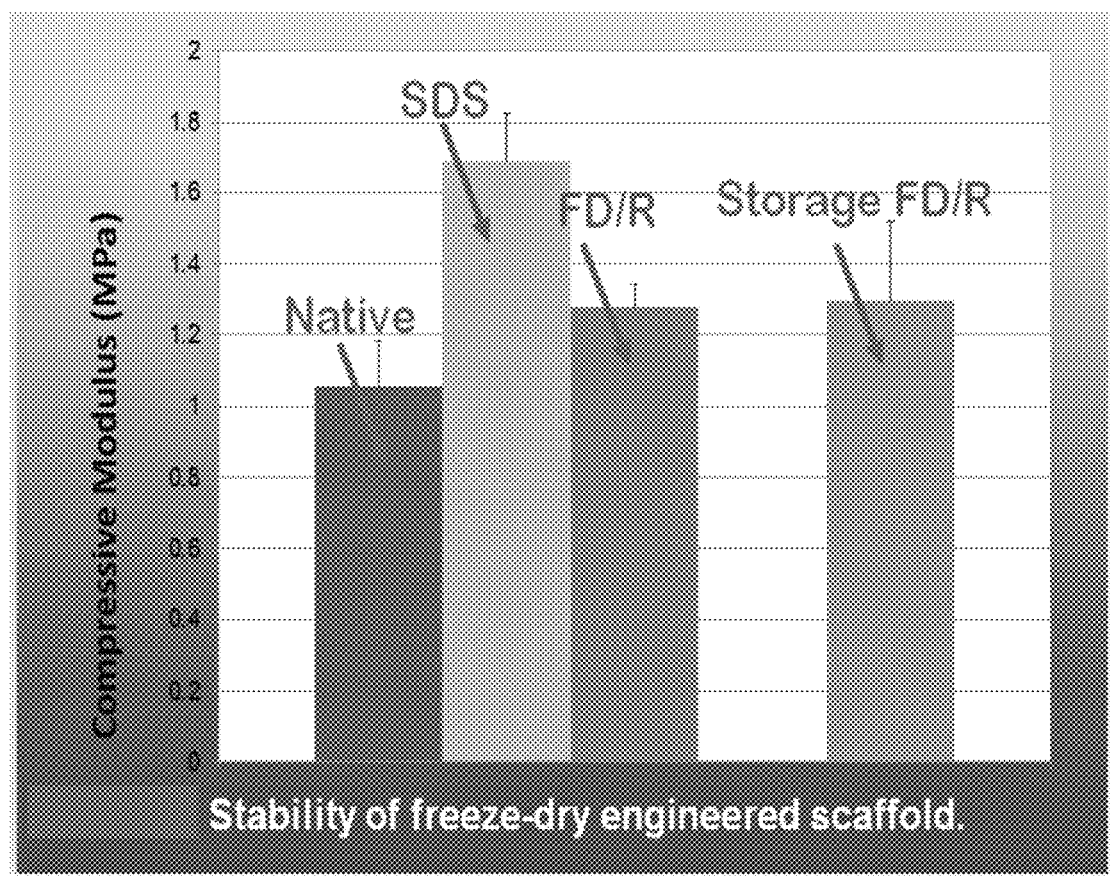
FIG. 1.3

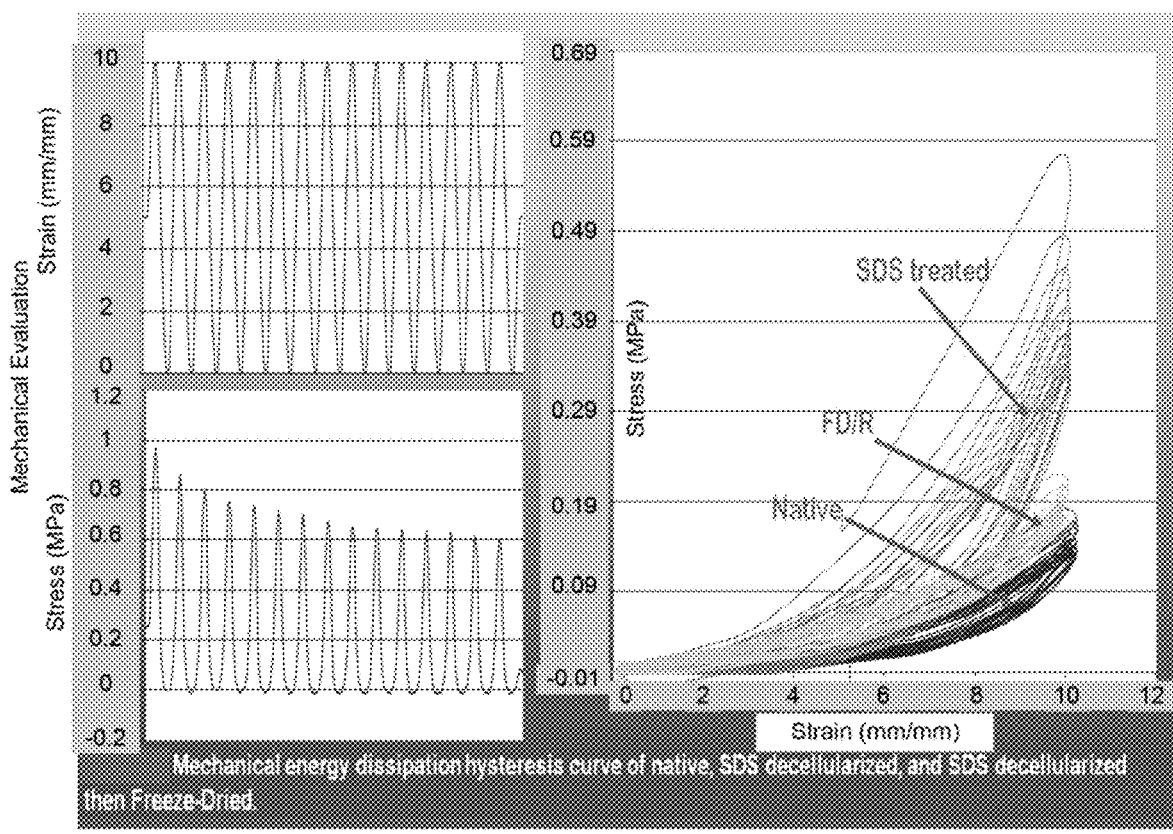
FIG. 1.4
FIG. 1.5

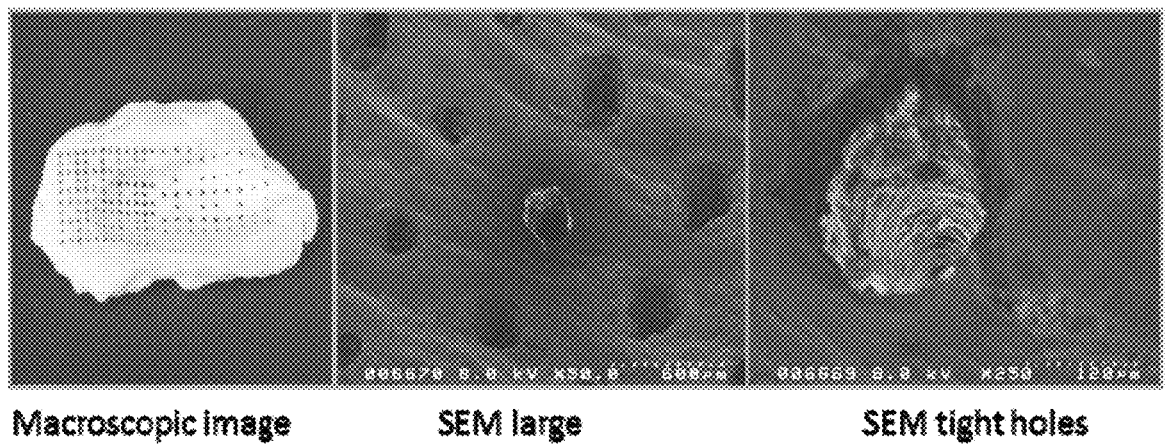
Macroscopic image　　SEM large　　SEM tight holes
FIG. 2.1
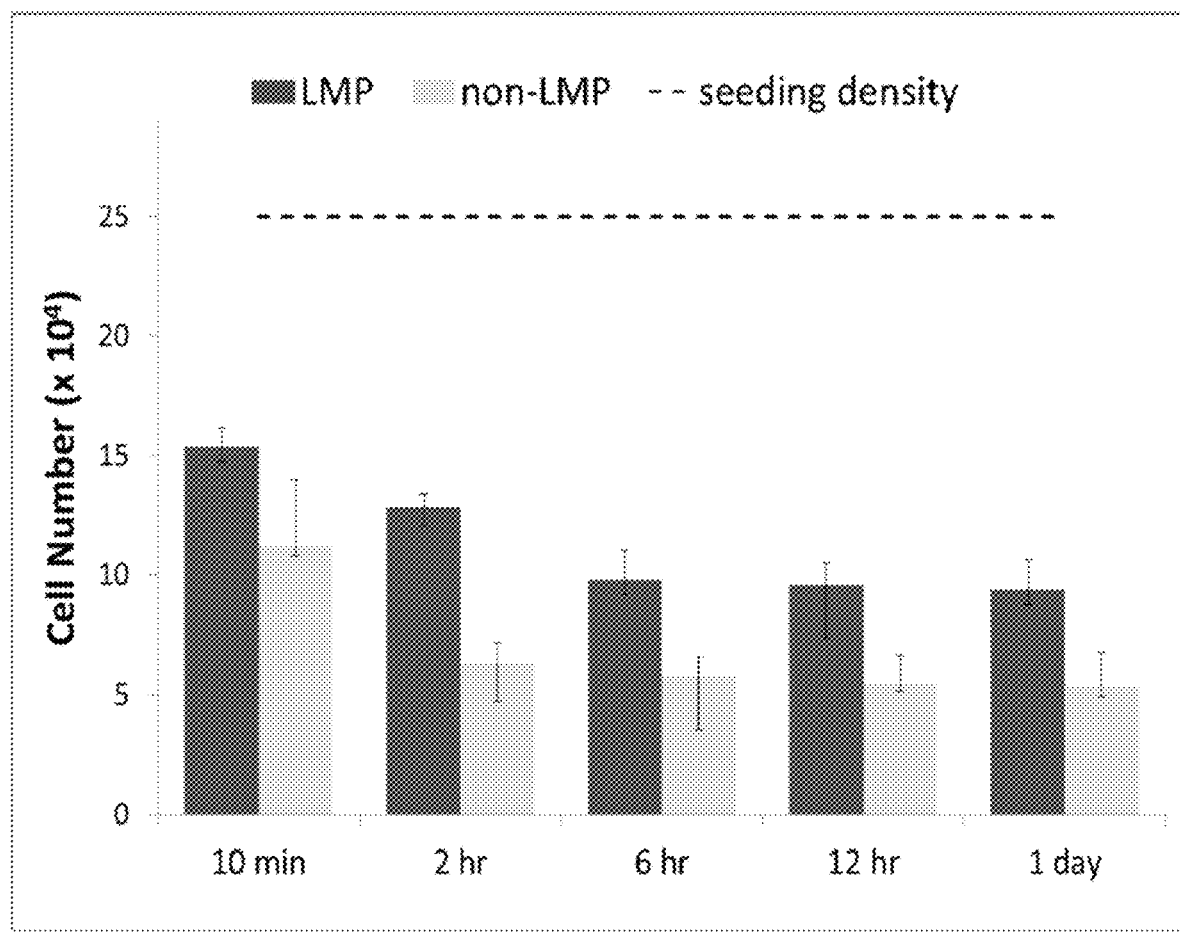
FIG. 2.2

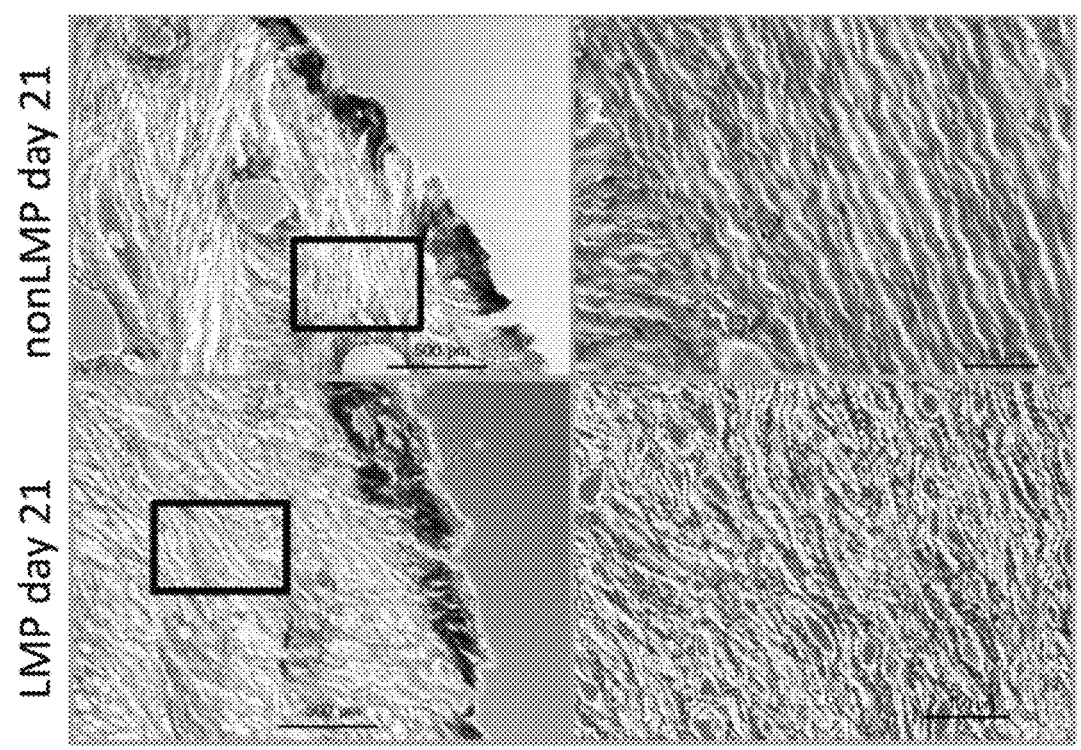
FIG. 2.3
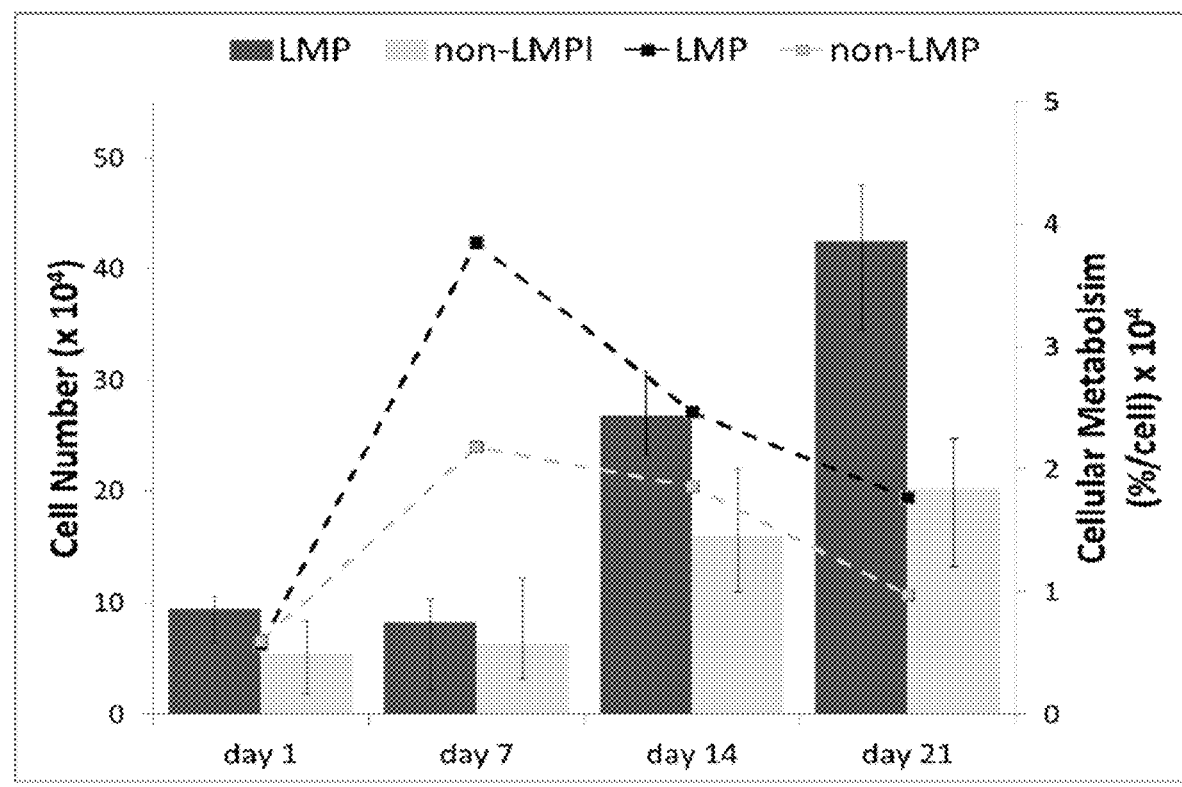
FIG. 2.4

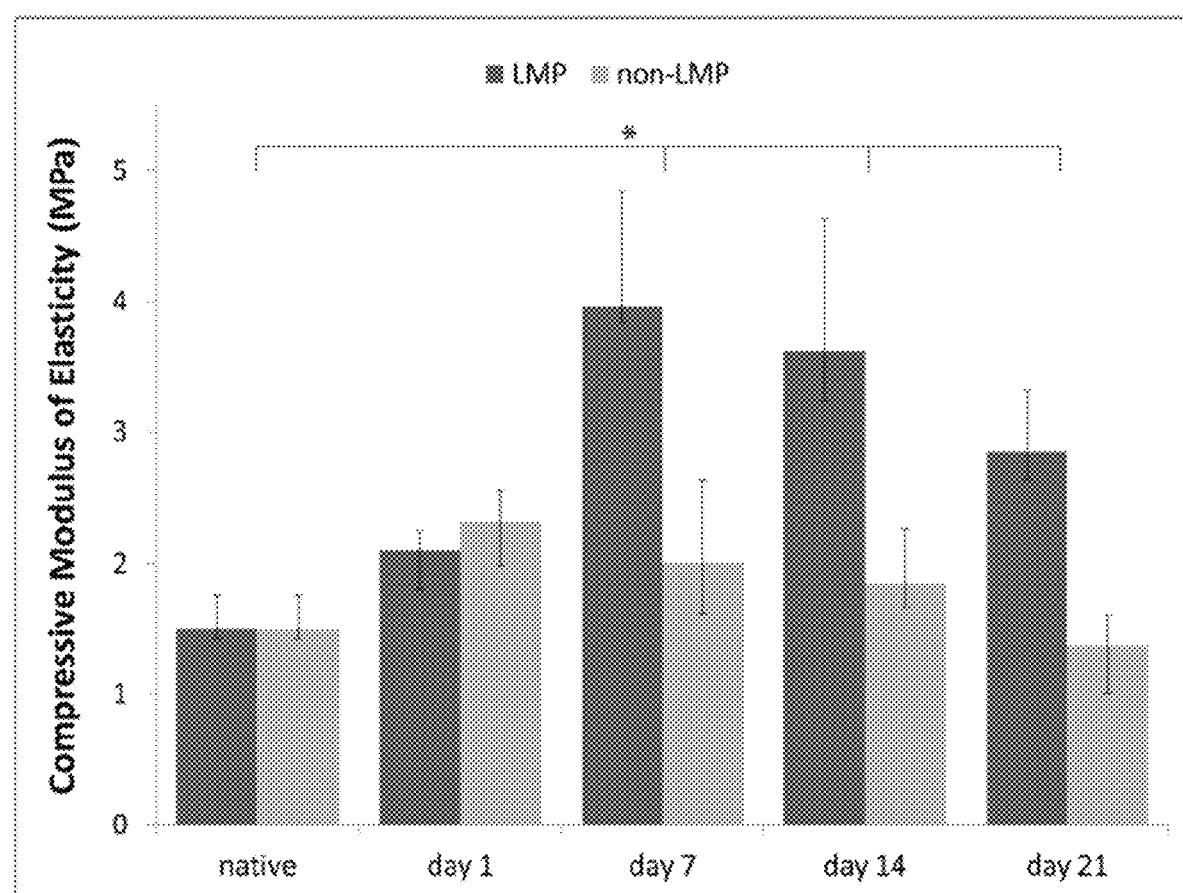
FIG. 2.5

IMPLANT MATERIALS FOR TMJ REPAIR, METHODS OF MAKING THE IMPLANT MATERIALS FOR TMJ REPAIR, AND METHOD OF USING IMPLANT MATERIALS FOR TMJ REPAIR

CLAIM OF PRIORITY TO RELATED APPLICATION

This application is a divisional application of U.S. Non-Provisional Application entitled "Implant Materials For TMJ Repair, Methods Of Making The Implant Materials For TMJ Repair, And Method Of Using Implant Materials For TMJ Repair", having application Ser. No. 14/363,538, filed Jun. 6, 2014, which is the 35 U.S.C. § 371 national stage of PCT Application No. PCT/US2012/068385, entitled "Implant Materials For TMJ Repair, Methods of Making the Implant Materials for TMJ Repair, and Method of Using Implant Materials for TMJ Repair" and filed Dec. 7, 2012, which is hereby incorporated by reference in its entirety, and which claims priority to, and the benefit of, U.S. Provisional Application No. 61/568,733, filed Dec. 9, 2011, which are hereby incorporated by reference in their entireties.

BACKGROUND

Fibrocartilage is a specialized tough and flexible tissue found in the TMJ disc of the jaw. These cartilage bumpers have a unique combination of tensile strength, compressive resistance, and elastic deformability that cushion the articulating skeletal structures surrounding them. Disease or damage to these discs deteriorates the energy distributive ability of the tissue, resulting in improper disc function. Neither the wide range of disc size and contour nor the complex mechanical abilities of fibrocartilage has yet to be replicated using synthetic matrix materials.

Epidemiological surveys have reported that up to 25% of the population exhibits symptoms of temporomandibular joint (TMJ) disorders. Despite the prevalence of TMJ disorders and the hefty cost of continual treatment of the painful symptoms, few treatment options for the morphological changes of the TMJ disc have been surveyed.

SUMMARY

In accordance with the purpose(s) of the present disclosure, as embodied and broadly described herein, embodiments of the present disclosure, in one aspect, relate to TMJ implantation materials and implants (e.g., temporomandibular joint (TMJ) disc), methods of making TMJ implantation materials and implants, methods of forming a TMJ implantation material or an implant, and the like.

In embodiments, the present disclosure includes a temporomandibular joint (TMJ) disc, among others, includes: a TMJ scaffold structure including a freeze-dried or previously freeze-dried, decellularized fibrocartilage tissue from a subject animal, the TMJ scaffold structure having a plurality of drilled holes in the scaffold structure.

According to aspects, in embodiments, the TMJ discs of the present disclosure has a compressive modulus and a peak stress value less than that of a corresponding sodium dodecyl sulfate (SDS) decellularized fibrocartilage tissue that has never been freeze-dried.

In embodiments, the present disclosure also provides A temporomandibular joint (TMJ) disc made by the following steps: obtaining a precursor TMJ scaffold structure comprising a fibrocartilage tissue from a subject animal; decellularizing the precursor TMJ scaffold structure to produce a decellularized TMJ scaffold structure; freeze drying the decellularized TMJ scaffold structure to form a freeze-dried TMJ scaffold structure; and after freeze drying, drilling a plurality of drilled holes in the decellularized, freeze-dried TMJ scaffold structure.

Other systems, methods, features, and advantages will be, or become, apparent to one with skill in the art upon examination of the following drawings and detailed description. It is intended that all such additional structures, systems, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1.1 are digital images (A-C) of a porcine TMJ (pTMJ) disc.

FIG. 1.2 illustrates a processed pTMJ.

FIG. 1.3 illustrates a graph showing the mechanical testing of TMJ samples.

FIG. 1.4 illustrates Table 1 which lists characteristic values for native, freeze-dried, and for samples at various rehydration times.

FIG. 1.5 illustrates graphs of mechanical energy dissipation hysteresis curve of native, SDS decellularized, and SDS decellularized then freeze-dried samples.

FIG. 2.1 illustrates images showing the controllable uniformity of laser micro-patterning the TMJ disc scaffold.

FIG. 2.2 illustrates a graph of cell adhesion over the initial 24 hours.

FIGS. 2.3 (images) and 2.4 (graph) illustrate cellular proliferation and metabolism over a 21 day culture.

FIG. 2.5 illustrates a graph showing the compressive modulus of elasticity evolution over 21 day culture.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Discussion

Exemplary embodiments of the present disclosure provide for TMJ implantation materials and implants (e.g., temporomandibular joint (TMJ) disc), methods of making TMJ implantation materials and implants, methods of forming a TMJ implantation material or an implant, and the like. In an embodiment, the TMJ material can serve as a replacement for a diseased or malfunctioning TMJ.

In general, an embodiment of the present disclosure includes a method where, the TMJ material is treated to remove antigens and/or other material (e.g., cells, proteins, and the like). In an embodiment, the TMJ material is from a subject animal. In an embodiment, the TMJ material is a porcine TMJ material, however, other animal TMJ material (e.g., direct human transplant/cadaver tissue, ovine, bovine, or other appropriately sized mammal) can be used consistent with the teachings of the present disclosure. In an embodiment, the TMJ material can be freeze-dried and/or have holes formed (e.g., laser drilled) in the TMJ material. In an embodiment, cells (e.g., human cells, stem cells, and the like) can be added to or incorporated into the TMJ material. Additional details are provided herein.

In an embodiment, the method for forming a temporomandibular joint (TMJ) disc includes obtaining a TMJ material (also referred to as "precursor TMJ scaffold structure") from an animal. In an embodiment, the precursor TMJ scaffold structure can include the TMJ disc, and/or ligaments. Subsequently, the precursor TMJ scaffold structure is decellularized to produce a decellularized TMJ scaffold structure. After decellularization, the decellularized TMJ scaffold structure can be freeze dried to from a freeze-dried TMJ scaffold structure. In an embodiment, the freeze-dried TMJ scaffold structure can be stored and processed (e.g., thawed, laser drilled, cultured with cells, and the like) at a later time.

In an embodiment, a plurality of holes (e.g., 2 to 1000) can be formed in the decellularized TMJ scaffold structure, prior to freeze-drying, just after freeze-drying, and/or after storage for a time frame after freeze-drying. In an embodiment, the freeze-dried TMJ scaffold structure can be cultured under conditions whereby the freeze-dried TMJ scaffold structure is colonized by a population of cells.

And prior to use, the freeze-dried TMJ scaffold structure is thawed to form a TMJ scaffold structure. In an embodiment, the culturing of the freeze-dried TMJ scaffold structure and the thawing process can occur at the same time or during overlapping time frames since as the freeze-dried TMJ scaffold structure thaws, the cells can be drawn (e.g., capillary forces) into the interior of the TMJ scaffold structure through the holes.

Now having described embodiments of the present disclosure in general, additional detail describing aspects of the present disclosure is presented. In an embodiment, the precursor TMJ scaffold structure can be formed by decellularizing the TMJ material to produce a decellularized TMJ scaffold structure. The term "decellularizing" or similar term can refer to removal or substantial (e.g., about 90% or more, about 95% or more, about 99% or more) removal of cells, proteins, antigens, and the like, from a tissue. In an embodiment, TMJ material is decellularized prior to freeze drying and/or formation of the holes. In an embodiment, the TMJ material is freeze dried after decellularizing. In an embodiment, the TMJ material is not decellularized prior to freeze drying and can be decellularized thereafter.

In an embodiment, the decellularizing process can take about 2 minutes to several days depending on the specific chemistry being used. In an embodiment, the precursor TMJ scaffold structure can be decellularized using sodium dodecyl (e.g., about 0.03 to 2% sodium dodecyl sulfate, where a larger concentration could be used if necessary), NaCl (e.g., about 4M NaCl, where a larger concentration could be used if necessary), peracetic acid (PAA) (e.g., about 0.1-1% PAA, where a larger concentration could be used if necessary), Triton X-100 (e.g., about 0.1 to 5% where a larger concentration could be used if necessary), or a variety of other surfactants, alcohols or other solubilizing agents, and a combination thereof. In an embodiment, the TMJ material can be decellularized using sodium dodecyl (e.g., about 0.03% sodium dodecyl sulfate).

In an embodiment, the TMJ material or the decellularized TMJ scaffold structure can include a plurality of holes. In an embodiment, the holes can be made through the TMJ tissue and/or into but not through the TMJ tissue. In an embodiment, the holes can be formed using a laser drilling technique, hole punching techniques, a manual drilling technique, and the like, or a combination thereof. In an embodiment, the holes can have a diameter of about 1 to 1000 micrometers or about 100 to 600 micrometers. In an embodiment, the holes can have a diameter on the nanometer scale (e.g., about 10 to 500 nm). In an embodiment, the plurality of holes can have the same diameter or can have two or more diameters, where the different diameter holes can be randomly placed or can be placed in a pattern. In an embodiment, one or more pairs of holes can be spaced apart by about 1 micrometer to 10 millimeters, where the spacing can be consistent or in a pattern or the holes can be randomly spaced. In an embodiment, the holes can be placed in one or more patterns in one area and placed randomly in another area. In an embodiment, the holes can have the same depth and in other embodiments, the holes can have two or more depths and optionally in one or more patterns in one area and placed randomly in another area.

In an embodiment, the holes can be formed at one or more times during the method (e.g., before and/or after freeze drying). In an embodiment, the holes can be formed in the TMJ tissue, prior to decellularization, after decellularization, before culturing, after culturing, before freeze drying, after freeze drying, and the like, and combinations thereof.

In an embodiment, a TMJ tissue having the holes can be advantageous to increase porosity (e.g., improve nutrient transport to improve tissue regeneration relative to structures without the holes), provide paths for the formation of microvessels, improve the transport condition of the material relative to tissue not including the holes, improve capacity to seed cells on or within the tissue relative to tissue not including the holes, improve capacity to promote cellular infiltration by providing a pathway for cells to move more freely relative to tissue not including the holes, encourage recellularization and/or vascularization, control mechanical compliance of the material, and combinations thereof.

In an embodiment, the TMJ material or the decellularized TMJ scaffold structure can be freeze dried. In an embodiment, the freeze drying process can include freezing the TMJ material or the decellularized TMJ scaffold structure to about 0 to −30° C. or about −20° C. and holding at that temperature for about 2 to 24 hours (or more) or about 12 hours. The frozen TMJ material or the decellularized TMJ scaffold structure can then undergo freeze-drying in a Millrock Bench-Top Freeze-Drier (Millrock Technologies Kingston, NJ) or similar freeze-drier at about −89° C. (+/−10° C.), at about 4 and 8 mT, for about 6 to 18 hour or about 12 hours.

In an embodiment, once the TMJ material or the decellularized TMJ scaffold structure has been freeze dried, it can be thawed out by placing in a suitable refrigerator, such as a 5° C. refrigerator, for a suitable time frame (e.g., about 1 hour or longer). In another embodiment, the TMJ material or the decellularized TMJ scaffold structure can also be thawed by using specific (controlled) temperature gradient devices to thaw (e.g., at a rate of 1° C. per minute) the sample. Once the sample is thawed to about room temperature, the sample can be used directly.

As mentioned above, appropriate human cells, stem cells, and the like, can be introduced to the TMJ material or the freeze-dried TMJ scaffold structure. In an embodiment, the cells can be introduced to the surface of the TMJ material or the freeze-dried TMJ scaffold structure but can also be added to the internal portions of the TMJ material or the freeze-dried TMJ scaffold structure by making holes into the TMJ tissue as described above. Also, different types of cells can be added to different internal and/or external areas of the TMJ material. Allowing the cells to migrate into the TMJ material or the freeze-dried TMJ scaffold structure to become part of the patient's natural body can improve the acceptance and function of the TMJ material or the freeze-dried TMJ scaffold structure.

In an embodiment, the decellularized TMJ scaffold structure or the freeze-dried TMJ scaffold structure can be cultured under conditions whereby the TMJ tissue is colonized by one or more populations of cells. In an embodiment, the population of cells can be selected from smooth muscle cells, stem cells, endothelial cells, fibroblasts, neuronal, skeletal muscle (others too), and a combination thereof. In an embodiment, the population of cells is a homogeneous population of cells or it can be a heterogenous population of cells. The term "conditions" means environmental conditions that replicate in vivo conditions. This can be under traditional static culture conditions (no dynamic movement) or conditioned in a bioreactor or similar device to mechanically condition cells.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

INTRODUCTION

Fibrocartilage is a specialized tough and flexible tissue found predominantly in the intervertebral discs of the spine, the menisci of the knee, and the Temporomandibular Joint (TMJ) disc of the jaw. These cartilage bumpers have a unique combination of tensile strength, compressive resistance, and elastic deformability that cushion the articulating skeletal structures surrounding them. Disease or damage to these discs deteriorate the energy distributive ability of the tissue, resulting in improper disc function. Neither the wide range of disc size and contour nor the complex mechanical abilities of fibrocartilage has yet to be replicated using synthetic matrix materials. These investigations evaluate the ability of a freeze-dried acellular xenogenic fibrocartilage scaffold to replicate the mechanical properties of the native tissue and effects of long term storage in the dried state.

Methods and Material:

The porcine TMJ (pTMJ) disc (FIG. 1.1) was chosen as a model fibrocartilage system due to its relevance to the human TMJ anatomy and function, as well as being established in dental research area.

Decellularization was accomplished using sodium dodecyl sulfate (SDS) solution with a 1% concentration agitated at 100 rpm on an orbital shaker plate for 24 hours. Freeze-drying was completed using a standard bench-top freeze dryer (Millrock Technologies Kingston, NJ) at −89 deg C. and between 4 and 8 mT for 12 hours then rehydrated in DI water at 20° C. for 12 hours.

Mechanical Testing was conducted using the Biomomentum MACH1 Mechanical Testing System. We evaluated the energy distributive ability of the pTMJ disc during compressive strain cyclic loading.

Statistical significance was established with one way ANOVA for each group and a p value of 0.05 (n=6).

Significance:

Epidemiological surveys have reported that up to 25% of the population exhibits symptoms of TMJ disorders. Despite the prevalence of TMJ disorders and the hefty cost of continual treatment of the painful symptoms, few treatment options for the morphological changes of the TMJ disc have been surveyed. These investigations explore the development of a naturally derived acellular TMJ disc construct capable of long duration storage. Freeze-Drying creates a stable long duration storage tissue engineered construct which maintain the morphological characteristics of the native TMJ disc.

An engineered disc may serve to alleviate pain associated with TMJ disorders, slow progression of TMJ tissue resorption due to improper load distribution, return normal jaw function to a previously impaired joint, and eliminate the need for costly recurrent treatment. An implant, or series of variously sized and shaped implants, that can be stably stored for extended time periods makes a natural tissue scaffold clinically feasible.

Experimental Set-Up:

These investigations examine the biomechanical impact of 1% sodium dodecyl sulfate (SDS) decellularization and a subsequent single freeze-dry/rehydrate (FD/R) cycle on pTMJ disc fibrocartilage (FIG. 1.2). After Freeze-Drying and rehydration mass change, dimensional change and histology were documented for each pTMJ test group. Stability of the freeze-dried acellular scaffolds was determined by keeping a group of scaffolds stored for a time of 6 months then rehydrating (stored FD/R) and mechanically testing as with the other test groups. From the mechanical data hysteresis loops, peak stresses, compressive and shear modulus values were computed Results:

Results have shown that the decellularization of the fibrocartilage tissue is destructive to the collagen fiber alignment. A change that results in distortion in the energy distributive ability of the scaffold.

Mechanical testing showed a large percentage of the hysteresis of the acellular disc is restored toward native values through the freeze-dry process (FIG. 1.3). Table 1 in FIG. 1.4 illustrates characteristic values for native, freeze-dried, and for samples at various rehydration times. FIG. 1.5 illustrates graphs of mechanical energy dissipation hysteresis curve of native, SDS decellularized, and SDS decellularized then freeze-dried samples. The compressive modulus of the FD/R fibrocartilage scaffolds is 1.270 MPa corresponding closely with the native TMJ disc value 1.054 MPa. The SDS decellularized samples were stiffer than the native or the FD/R discs with a compressive modulus of 1.710 MPa and a peak stress of 0.567 MPa in comparison to 0.133 MPa and 0.185 MPa for the native and FD/R samples respectively. We hypothesize that restoration of the mechanical properties of the FD/R disc toward the native values from the SDS decellularized is due to the dehydration step in the Freeze-Drying process. Mechanical stability was established with the acellular fibrocartilage scaffold over long duration storage by storing the pTMJ disc in its freeze-dried state for 6 months. Then the discs were rehydrated and tested as described for previous samples. No significant rehydration, mechanical, or histological difference was observed between the single FD/R disc and the stored FD/R discs.

Conclusion:

It is important in the generation of a tissue engineered TMJ disc that the implant be clinically feasible and retain the characteristics of the healthy native disc. These experimental works support the theory that Freeze-drying fibrocartilage creates a long term storage implant which preserves mechanical integrity and ECM structure. The freeze-drying process acts toward restoration of the collagen microenvironment distorted by SDS decellularization, in which it is hypothesized that the disruption of hydrogen bonding by SDS is restored during the compaction of the scaffold during freeze-drying. The freeze-dried porcine TMJ fibrocartilage disc maintains deformation resistance and energy dissipation capabilities of the native TMJ disc under physiologically relevant loading conditions.

Example 2

FIG. 2.1 illustrates images showing the controllable uniformity of laser micro-patterning the TMJ disc scaffold. The sodium dodecyl sulfate (SDS) decellularized TMJ disc scaffolds were progressively frozen first to −20° C. for 6 hours followed by −80° C. for 18 hours. After the freezing cycle, 24 hours in total, the scaffolds were lyophilized (freeze-dried) for 24 hours at −84° C. in vacuum less than 8 mTorr (<1.66 Pa) using a bench top freeze-drier (Millrock Technology, Kingston, NY). Once sublimation of the ice crystals was completed the scaffolds were laser worked using a 40W $CO_2$ laser engraver (Full Spectrum Laser, Las Vegas, NV). The pattern printed incorporated 120 μm holes at 480 μm centerline-to-centerline separation in an 8×8 grid in the center zone of the disc.

FIG. 2.2 illustrates a graph of cell adhesion over the initial 24 hours. Cells isolated from human umbilical cord (hUC) Wharton's Jelly matrix were seeded onto 120 μm holes size LMP TMJ disc scaffold at a seeding density of 900 cells/$mm^2$ and evaluated using the Quanti-iT PicoGreen DNA Quantification assay (Invitrogen, Oregon, USA) for adhesion over the initial 24 hours of culture (5% $CO_2$ and 37° C.). To isolated cells full term placental tissues were collected at Shands Hospital Women's Delivery Ward (Gainesville, Fl)

and the Wharton's Jelly of the hUC dissected and cut into 2-3 mm cubes cultured in t-25 cell culture flask (Falcon) for 2-3 weeks with media change every 3 days then passaged twice to provide highly proliferative p-3 human cells for further use. The Wharton's Jelly derived cells were exposed to standard culture media consisting of Dulbecco's Modified Eagle's Medium (DMEM, Invitrogen, Oregon, USA) supplemented with 1% penicillin streptomycin (Gibco Life Technologies, Grand Island, NY) and 10% fetal bovine serum complex (FetalPlex, Genimini Bio-Products, West Sacramento, CA). At 24 hours more cells remain attached to the surface of the LMP scaffold likely due to increased surface roughness as a result of the laser working.

FIGS. 2.3 (images) and 2.4 (graph) illustrate cellular proliferation and metabolism over a 21 day culture. Cellular proliferation was assessed using the Quanti-iT PicoGreen DNA Quantification assay (Invitrogen, Oregon, USA). Metabolic activity per cell was determined by measurement of metabolic reduction of the media using a resazurin salt assay, against a calibration curve of the same cell lineage. The LMP punch has greater sustained cell proliferation than the non-LMP over the course of culture, and that the metabolic activity per cell is greater in the LMP punch as well. These results indicate that the increased surface area and mass transport due to the pores enables greater cell activity over the initial scaffold remodeling period.

FIG. 2.5 illustrates a graph showing the compressive modulus of elasticity evolution over 21 day culture. 6 mm central zone laser micro-patterned scaffold punches were cyclically compressed to 10% strain. The mechanical consequence of cellular integration through the thickness of the scaffold demonstrates that the non-LMP scaffold becomes more elastic, with a linear geometric decreasing trend, while the LMP scaffold is strengthened during initial cell incorporation (between day 1 and day 7) before continuing in the typical scaffold mechanical weakening seen during static culture.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of the numerical value, or more of the numerical value(s) being modified.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

I claim the following:

1. A temporomandibular joint (TMJ) disc, comprising:
a TMJ scaffold structure comprising a freeze-dried, decellularized fibrocartilage tissue from a subject animal, the TMJ scaffold structure having a plurality of drilled holes in the scaffold structure,
wherein the TMJ scaffold structure is obtained from a precursor TMJ scaffold structure comprising said fibrocartilage tissue from a subject animal,
wherein the freeze-dried, decellularized fibrocartilage tissue has a compressive modulus and a peak stress value less than that of a corresponding sodium dodecyl sulfate (SDS) decellularized fibrocartilage tissue that has never been freeze-dried.

2. The TMJ disc of claim 1, further comprising one or more populations of added cells, wherein a portion of the cells are in the holes of the TMJ scaffold structure.

3. The TMJ disc of claim 2, wherein the population of cells is selected from the group consisting of: stem cells, endothelial cells, smooth muscle cells, fibroblasts, and combinations thereof.

4. The TMJ disc of claim 2, wherein the population of cells is a homogeneous population of cells.

5. The TMJ disc of claim 2, wherein the population of cells is a heterogenous population of cells.

6. The TMJ disc of claim 1, wherein the TMJ scaffold structure is substantially free of non-TMJ tissue.

7. The TMJ disc of claim 1, wherein the holes have a diameter of about 1 to 500 micrometers.

8. The TMJ disc of claim 1, wherein one or more pairs of holes are spaced by about 1 micrometer to 10 millimeters.

9. The TMJ disc of claim 1, wherein the holes are through the scaffold structure, the holes are only partially through the scaffold structure, or a portion of the holes are through the scaffold structure and a portion of the holes are only partially through the scaffold structure.

10. The TMJ disc of claim 1, wherein the TMJ scaffold structure is a porcine TMJ fibrocartilage tissue.

11. The TMJ disc of claim 1, wherein the fibrocartilage tissue comprises a TMJ disc from the subject animal.

12. The TMJ disc of claim 1, wherein the subject animal is a mammal selected from the group of mammals consisting of: humans, porcines, ovines, and bovines.

13. The TMJ disc of claim 1, wherein the fibrocartilage tissue is a xenogenic fibrocartilage tissue.

14. The TMJ disc of claim 1, wherein the TMJ scaffold structure is rehydrated.

15. The TMJ disc of claim 1, wherein the decellularized fibrocartilage tissue was decellularized with sodium dodecyl sulphate or sodium chloride.

* * * * *